United States Patent [19]
Brecher

[11] Patent Number: 4,958,393
[45] Date of Patent: Sep. 25, 1990

[54] ORTHOPEDIC CRADLE

[76] Inventor: Arie Brecher, Eilat St. 23, Holon 58310, Israel

[21] Appl. No.: 809,303

[22] Filed: Dec. 16, 1985

[30] Foreign Application Priority Data

Dec. 27, 1984 [IL] Israel ........................................ 73956

[51] Int. Cl.⁵ .............................................. A47C 20/00
[52] U.S. Cl. ........................................ 5/431; 5/93.1; 128/870
[58] Field of Search .................... 5/443, 431, 93 R, 94, 5/102, 98 R; 128/80 R, 78, 68, 134, 870; 269/328; 297/487, 488

[56] References Cited

U.S. PATENT DOCUMENTS

| | | | |
|---|---|---|---|
| D. 259,274 | 5/1981 | Humes | 5/443 |
| 3,034,502 | 5/1962 | Lund | 128/134 |
| 3,339,544 | 9/1967 | Kravitz | 5/443 |
| 3,423,773 | 1/1969 | Yamate | 5/443 |
| 3,431,020 | 3/1969 | Tyndall | 5/443 |
| 3,563,600 | 2/1971 | Converse | 297/467 |
| 3,659,865 | 5/1972 | Nothacker | 297/488 |
| 3,729,752 | 5/1973 | Huggins | 5/93 R |
| 4,108,168 | 8/1978 | Craig | 128/134 |
| 4,359,045 | 11/1982 | Cozzi | 5/431 |
| 4,441,221 | 4/1984 | Enste et al. | 5/431 |

FOREIGN PATENT DOCUMENTS

| | | | |
|---|---|---|---|
| 2330935 | 1/1974 | Fed. Rep. of Germany | 297/488 |
| 2714272 | 10/1978 | Fed. Rep. of Germany | 128/78 |

Primary Examiner—Gary L. Smith
Assistant Examiner—Flemming Saether
Attorney, Agent, or Firm—Benjamin J. Barish

[57] ABSTRACT

An orthopedic cradle for aiding in the prevention of hip articulation disorders in infants, comprises, bottom, foot, head and side walls, a post secured at its lower end to the bottom wall at an intermediate location on its central longitudinal axis, and a transverse bar joined at its mid-portion to the upper end of the post and at its opposite ends to the side walls. The post and transverse bar define a pair of sockets for receiving the two legs of the infant to form an angle of 60°–90° with respect to the longitudinal axis of the infant's torso.

19 Claims, 1 Drawing Sheet

U.S. Patent       Sep. 25, 1990       4,958,393
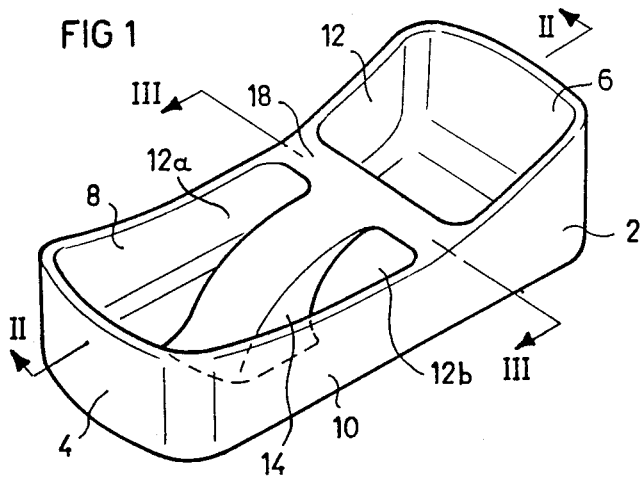
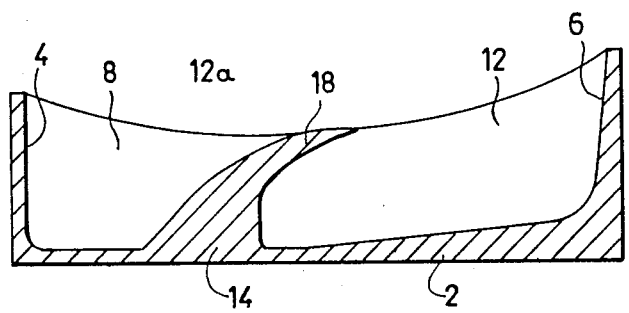
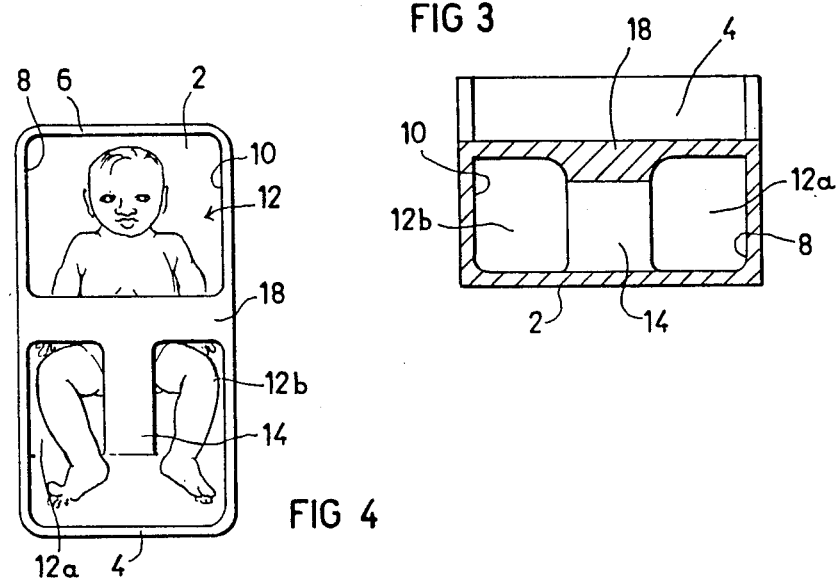

ORTHOPEDIC CRADLE

BACKGROUND OF THE INVENTION

The present invention relates to orthopedic cradles, and particularly to such cradles for aiding in the prevention of hip articulation disorders in infants.

There are two types of infant hip articulation disorders with which the invention is particularly concerned, namely: (1) congenital dislocation of the hip (called "CDH"), which can be diagnosed by clinical examination and also by X-ray examination of the pelvis and hips; and (2) displasia of the hip articulations, which usually can be diagnosed only by X-ray examination. The treatment given in both cases, except late-discovered CDH, is to keep the infant's legs in a wide open position. A number of devices are known for rendering this treatment, including the Craig, Von Rosen and Ilfeld attachments, the Pavlik-harness, and the Frejka-pillow. These devices are used to fix the hips with the legs in a wide open position after a CDH or displasia condition of any severity has been found to be present.

Such hip articulation disorders occur with such frequency that when an infant is discharged from the maternity department of a hospital, it is frequently suggested that the mother use a "double-diaper", particularly when a hip disorder is suspected, in order to impose on the baby a wide openlegged position to prevent a dislocation or displasia of the hip articulations. However, a double-diaper is frequently ineffective to prevent the above-described hip articulation disorders. Moreover, the "double-diaper" subjects the infant to considerable discomfort and interferes with the free sensation of the legs.

SUMMARY OF THE INVENTION

An object of the present invention is to provide an orthopedic cradle for aiding in the prevention of hip articulation disorders of the foregoing type, which cradle is more effective than the "double-diaper", subjects the infant to considerably less discomfort, and does not interfere with the free sensation of the legs as compared to the "double-diaper".

According to the present invention, there is provided an orthopedic cradle for aiding in the prevention of hip articulation disorders in infants, the cradle including: a bottom wall for resting on a horizontal surface, a foot wall at the foot of the cradle, a head wall at the head of the cradle, and a pair of side walls joined to the bottom, foot and head walls, the foot, head and side walls being of sufficient height to define a compartment for holding the infant against falling out when the infant is received therein in a substantially horizontal position. with the infant's head adjacent to the head wall and the infant's feet adjacent to the foot wall; characterized in that the cradle further includes a post secured at its lower end to the bottom wall at an intermediate location thereof on its central longitudinal axis, and a transverse bar joined at its mid-portion to the upper end of the post and at its opposite ends to the pair of side walls, the post and transverse bar defining a pair of sockets for receiving the two legs of the infant with the post spreading the two legs apart to force the infant to lie in a wide open-legged position.

Preferably, the post has a sufficient width transverly of the cradle to spread apart the legs of the infant disposed within the cradle to an angle of 60° to 90° with respect to the longitudinal axis of the infant's torso.

The orthopedic cradle of the present invention is intended particularly for use during the first three-four months of the infant's life. Since the orthopedic cradle forces the infant to lie in a wide open-legged position, it contributes greatly to the prevention of hip articulation disorders, but at the same time it does not subject the infant to the discomfort of the double-diaper; moreover, it does not interfere with the free sensation of the legs. The novel orthopedic cradle is particularly useful for preventing hip articulation disorders, but it may also be used on occasion for the treatment of such disorders. Further, the infant would normally be placed in the orthopedic cradle on his back (supine position), but when the infant is not under the observation of an adult, for example during the night, the infant may be placed on its stomach in the cradle. This positioning of the ifant is also effective to prevent and/or to treat cases of internal rotation of the leg or foot.

Further features and advantages of the invention will be apparent from the description below.

BRIEF DESCRIPTION OF THE DRAWINGS

The invention is herein described, by way of example only, with reference to the accompaying drawings, wherein:

FIG. 1 illustrates one form of orthopedic cradle constructed in accordance with the present invention;

FIG. 2 is an longitudinal sectional view along lines II—II of FIG. 1;

FIG. 3 is a transverse sectional view along lines III-—III of FIG. 1; and

FIG. 4 is a top plan view illustrating the orthopedic cradle of FIG. 1, as occupied by an infant, in aiding in the prevention of hip articulation disorders during the first few months of the infant's life.

DESCRIPTION OF A PREFERRED EMBODIMENT

The orthopedic cradle illustrated in the drawings comprises a bottom wall 2 for resting on a flat horizontal surface, an anterior or foot wall 4 at the foot end of the cradle, a posterior or head wall 6 at the head end of the cradle, and a pair of lateral or side walls, 8, 10 joined to the foregoing walls. As in the usual cradle the foot, head and side walls are of sufficient height to define a compartment 12 for holding the infant against falling out when the infant is received therein in a substantially horizontal position with the infant's head adjacent to the head wall 6 and the infant's feet adjacent to the foot wall 4.

The illustrated cradle further includes a center post or saddle 14 secured at its lower end to the cradle at an intermediate location thereof on its central longitudinal axis. The cradle further includes a transverse bar or arch 18 joined at its mid-portion to the upper end of center post 14, and at its opposite ends to the pair of side walls 8, 10.

Center post 14 and transverse bar 18 together define a pair of sockets 12a, 12b for receiving the two legs of the infant with the post spreading the two legs apart. As shown particularly in FIG. 2, post 14 has a width transversely of the cradle to spread the infant's legs widely apart, preferably to an angle of between 60° and 90° with respect to the longitudinal axis of the infant's torso.

Center post 14 is of tapering thickness in the direction of the longitudinal axis of the cradle, being largest at its base joined to cradle, and smallest at its upper end joined to the transverse bar 18. As best seen in FIG. 2, post 14 is located closer to the foot wall 4 of the cradle than to the head wall 6, and the head edge of the transverse bar 18 is located closer to the head wall 6 than to the foot wall 4. The post is of curved configuration, curving gradually from a substantially right angle at its juncture with the bottom wall 2 of the cradle, through an arc of approximately 90° to its juncture with transverse bar 18.

As also best seen in FIG. 2, the inside face of the cradle is downwardly inclined from the head wall 6 in the direction towards the foot wall 4 to form an oblique floor. The angle of inclination is preferably from 2°-10°, from head wall 6 to the juncture of center post 14 with the bottom wall 2 of the cradle.

It will thus be seen that when the infant is placed in compartment 12 of the cradle, with its head adjanet to head wall 6, its feet are received within the two sockets 12a, 12b on the opposite sides of center post 14. The post thus forces the infant to lie in a wide open-legged position, with each leg being at an angle of between 60° and 90° with respect to the longitudinal axis of the infant's torso. The transverse bar 18 prevents the infant from pulling its legs out of the spaces 12a, 12b, while the inclination of the cradle at the head end of the cradle urges the infant towards the transverse bar 18 and thereby prevents the infant from moving away from the transverse bar and post 14.

The illustrated orthopedic cradle is preferably constructed of a lightweight, rigid, plastic material which is non-toxic to the infant, with all the walls, as well as the center post 14 and transverse bar 18, integrally formed together as one integral unit. As one example, the cradle may have the following dimensions: Length, 75 cm; width, 35 cm; height of upper edge of crossbar, 15 cm; thickness of base of center post 14 in direction of longitudinal axis, 15 cm; width of center post 14 in direction transversely to longitudinal axis, 15 cm; distance of front edge of the center post from foot wall 4, 15 cm; distance of the head end of transverse bar 18 from the head wall 6, 32 cm; and angle of inclination of the head end of the bottom wall 5°.

It will be appreciated that the foregoing dimensions are set forth purely for purposes of example.

While the invention has been described with respect to one preferred embodiment, many other variations, modifications and applications of the invention may be made.

What is claimed is:

1. An orthopedic cradle for supporting an infant in a horizontal position while aiding in the prevention of hip articulation disorders in the infant, said cradle being of the basket-type and including: a bottom wall for resting on a horizontal surface, a foot wall at the foot end of the cradle, a head wall at the head end of the cradle, and a pair of side walls joined to said bottom, foot and head walls; said foot, head and side walls being of sufficient height to define a compartment for holding the infant, indepently of any other holding means, against falling out when the infant is received therein in a substantially horizontal position with the infant's head adjacent to the head wall and the infant's feet adjacent to the foot wall; characterized in that said cradle further includes a post secured at its lower end to the bottom wall at an intermediate location thereof on its central longitudinal axis, and a transverse bar joined at its mid-portion to the upper end of said post and at its opposite ends to said pair of side walls, said post and transverse bar defining a pair of sockets for receiving the two legs of the infant with the post spreading the two legs apart to force the infant to lie horizontally in a wide open-legged position; said post having a width transversely of the cradle sufficient to spread apart the legs of the infant to an angle of between 60° to 90° with respect to the longitudinal axis of the infant's torso.

2. The orthopedic cradle according to claim 1, wherein said post is located closer to the foot wall than to the head wall, and said transverse bar is located closer to the head wall than to the foot wall.

3. The orthopedic cradle according to claim 2, wherein said post is of curved configuration, curving gradually from its juncture with the bottom wall to its juncture with said transverse bar.

4. The orthopedic cradle according to claim 3, wherein said post is curved from a substantially right angle juncture with the bottom wall through an arc of approximately 90° to its juncture with the transverse bar.

5. The orthopedic cradle according to claim 1, wherein the inside face of said bottom wall is downwardly inclined from the head wall in the direction toward the foot wall.

6. The orthopedic cradle according to claim 5, wherein said bottom wall is downwardly inclined at an angle of 2-10° from the head wall to the juncture of said post with the bottom wall.

7. The orthopedic cradle according to claim 6, wherein said angle of inclination of the bottom wall is approximately 5°.

8. The orthopedic cradle according to claim 1, wherein said post and transverse bar are formed integrally with said bottom, foot, head and side walls.

9. The orthopedic cradle according to claim 5, wherein said bottom wall is downwardly inclined at an angle of 2-10° from the head wall to the juncture of said post with the bottom wall.

10. An orthopedic cradle for supporting an infant in a horizontal position while aiding in the prevention of hip articulation disorders in the infant, said cradle being of the basket-type and including: a bottom wall for resting on a horizontal surface, a foot wall at the foot end of the cradle, a head wall at the head end of the cradle, and a pair of side walls joined to said bottom, foot and head walls; said foot, head and side walls being of sufficient height to define a compartment for holding the infant, indepently of any other holding means, against falling out when the infant is received therein in a substantially horizontal position with the infant's head adjacent to the head wall and the infant's feet adjacent to the foot wall; characterized in that said cradle further includes a post secured at its lower end to the bottom wall at an intermediate location thereof on its central longitudinal axis, and a transverse bar joined at its mid-portion to the upper end of said post and at its opposite ends to said pair of side walls, said post and transverse bar defining a pair of sockets for receiving the two legs of the infant with the post spreading the two legs apart to force the infant to lie horizontally in a wide open-legged position; said post being of tapering thisckness in the direction of the longitudinal axis of the cradle, being largest at its base joined to the bottom wall and smallest at its upper end joint to said transverse bar.

11. An orthopedic cradle for supporting an infant in a horizontal position while aiding in the prevention of hip articulation disorders in the infant, said cradle being of the basket type and including:

a bottom wall for resting on a horizontal source, a foot wall at the foot end of the cradle, a head wall at the head end of the cradle, and a pair of side walls joined to said bottom, foot and head walls; said foot, head and side walls being of sufficient height to define a compartment for holding the infant, independently of any other holding means, against falling out when the infant is received therein in a substantially horizontal position with the infant's head adjacent to the head wall and the infant's feet adjacent to the foot wall;

a post secured at its lower end to the bottom wall at an intermediate location thereof on its central longitudinal axis, said post being of tapering thickness in the direction of the longitudinal axis of the cradle, being largest at its base joined to the bottom wall and smallest at its upper end;

and a transverse bar joined at its mid-portion to the upper end of said post and at its opposite ends to said pair of side walls, said post and transverse bar defining a pair of sockets for receiving the two legs of the infant with the post spreading the two legs apart to force the infant to lie horizontally in a wide open-legged position.

12. The orthopedic cradle according to claim 11, wherein said post has a width of transversely of the cradle sufficeint spread apart the legs of the infant to an angle of between 60° and 90° with respect to the longitudinal axis of the infant's torso.

13. The orthopedic cradle according to claim 11, wherein said post is located closer to the foot wall than to the head wall, and said the head edge of transverse bar is located closer to the head wall than to the foot wall.

14. The orthopedic cradle according to claim 13, wherein said post is of curved configuration, curving gradually from its juncture with the bottom wall to its juncture with said transverse bar.

15. The orthopedic cradle according to claim 14, wherein said post is curved from a substantially right angle juncture with the bottom wall through an arc of approximately 90° to its juncture with the tranverse bar.

16. The orthopedic cradle according to claim 11, wherein the inside face of said bottom wall is downwardly inclined from the head wall in the direciton toward the foot wall.

17. An orthopedic cradle for supporting an infant in a horizontal position while aiding in the prevention of hip articulation disorders in the infant, said cradle being of the basket type and including:

a bottom wall for resting on a horizontal source, a foot wall at the foot end of the cradle, a head wall at the head end of the cradle, and a pair of side walls joined to said bottom, foot and head walls; said foot, head and side walls being of sufficient height to define a compartment for holding the infant, independently of any other holding means, against falling out when the infant is received therein in a substantially horizontal position with the infant's head adjacent to the head wall and the infant's feet adjacent to the foot wall;

a post secured at its lower end to the bottom wall at an intermediate location thereof on its central longitudinal axis;

and a transverse bar joined at its mid-portion to the upper end of said post and at its opposite ends to said pair of side walls, said post and transverse bar defining a pair of sockets for receiving the two legs of the infant with the post spreading the two legs apart;

said bottom wall being downwardly inclined at an angle of 2-10° from the head wall to the juncture of said post with the bottom wall.

18. The orthopedic cradle according to claim 17, wherein said post has a width transversely of the cradle sufficient to spread apart the legs of the infant to an angle between 60° and 90° with respect to the longitudinal axis of the infant's torso.

19. The orthopedic cradle according to claim 17, wherein said post is of tapering thickness in the direction of the longitudinal axis of the cradle, being largest at its base joined to the bottom wall and smallest at its upper end joined to said tranverse bar.

* * * * *